(12) United States Patent
Vanderbilt

(10) Patent No.: US 6,657,032 B2
(45) Date of Patent: Dec. 2, 2003

(54) HIGH REFRACTIVE INDEX HYDROGEL COMPOSITIONS FOR OPHTHALMIC IMPLANTS

(75) Inventor: David P. Vanderbilt, St. Louis, MO (US)

(73) Assignee: Bausch & Lomb Incorporated, Rochester, NY (US)

( * ) Notice: Subject to any disclaimer, the term of this patent is extended or adjusted under 35 U.S.C. 154(b) by 0 days.

(21) Appl. No.: 09/974,932

(22) Filed: Oct. 10, 2001

(65) Prior Publication Data

US 2002/0042483 A1 Apr. 11, 2002

Related U.S. Application Data

(62) Division of application No. 09/209,552, filed on Dec. 11, 1998, now Pat. No. 6,329,485.

(51) Int. Cl.$^7$ .................. C08F 220/68; A61F 2/16
(52) U.S. Cl. .................. 526/320; 526/264; 526/307.5; 526/307.7; 526/317.1; 526/318.1; 526/319; 526/329.2; 623/6.11
(58) Field of Search .................. 526/264, 307.5, 526/307, 7, 320, 318.1, 317.1, 319, 328.5, 307.7, 329.2; 623/6.11

(56) References Cited

U.S. PATENT DOCUMENTS

| | | | | |
|---|---|---|---|---|
| 5,217,491 A | | 6/1993 | Vanderbilt | 623/6 |
| 5,233,007 A | | 8/1993 | Yang | |
| 5,236,970 A | | 8/1993 | Christ et al. | |
| 5,258,024 A | | 11/1993 | Chavel et al. | 623/5 |
| 5,290,892 A | | 3/1994 | Namdaran et al. | 526/259 |
| 5,326,506 A | | 7/1994 | Vanderbilt | 264/1.7 |
| 5,331,073 A | | 7/1994 | Weinschenk, III et al. | |
| 5,359,021 A | | 10/1994 | Weinschenk, III et al. | 526/264 |
| 5,376,694 A | | 12/1994 | Christ et al. | |
| 5,403,901 A | | 4/1995 | Namdaran et al. | 526/259 |
| 5,420,213 A | | 5/1995 | Yang | |
| 5,433,746 A | | 7/1995 | Namdaran et al. | 623/6 |
| 5,480,950 A | | 1/1996 | Wang et al. | 526/258 |
| 5,494,946 A | | 2/1996 | Christ et al. | |
| 5,512,609 A | | 4/1996 | Yang | |
| 5,623,029 A | | 4/1997 | Yang | |
| 5,661,195 A | | 8/1997 | Christ et al. | |
| 5,674,960 A | | 10/1997 | Namdaran et al. | 526/259 |
| 5,693,095 A | | 12/1997 | Freeman et al. | 623/6 |
| 5,717,049 A | | 2/1998 | Liao et al. | 526/304 |
| 5,861,031 A | | 1/1999 | Namdaran et al. | |
| 5,891,931 A | | 4/1999 | Leboeuf et al. | 522/64 |
| 6,036,891 A | * | 3/2000 | Liao et al. | 252/588 |
| 6,140,438 A | * | 10/2000 | Ojio et al. | 526/264 |
| 6,267,784 B1 | * | 7/2001 | Benz et al. | 623/6.59 |
| 6,329,485 B1 | * | 12/2001 | Vanderbilt | 526/317.1 |

FOREIGN PATENT DOCUMENTS

| | | | | |
|---|---|---|---|---|
| EP | 0 869 138 A | 10/1998 | | |
| FR | 2 757 065 A | 6/1998 | | |
| WO | WO 94/07686 | 4/1994 | | B29D/11/00 |
| WO | WO 96 40303 A | 12/1996 | | |
| WO | WO 97 24382 | 7/1997 | | |

OTHER PUBLICATIONS

Patent Abstracts of Japan (vol. 1999, No. 08) Publication No. 11056999 Publication Date: Feb. 3, 1999 Title: Soft Intra–Eye Lens Material.

* cited by examiner

*Primary Examiner*—Tatyana Zalukaeva
(74) *Attorney, Agent, or Firm*—Rita D. Vacca

(57) ABSTRACT

Optically transparent, high refractive index hydrogels and intraocular lenses fabricated therefrom. The preferred hydrogels have a refractive index of 1.45 or above and a water content of approximately 5 to 30 percent by weight.

23 Claims, No Drawings

HIGH REFRACTIVE INDEX HYDROGEL COMPOSITIONS FOR OPHTHALMIC IMPLANTS

This application is a divisional application of prior application Ser. No. 09/209,552 filed Dec. 11, 1998 now U.S. Pat. No. 6,329,485.

FIELD OF THE INVENTION

The present invention relates to novel ophthalmic lens materials and a method for making and using the same. More particularly, the present invention relates to soft, optically transparent, high refractive index hydrogel materials particularly suited for use in the production of intraocular lenses, and a method for manufacturing and using the same.

BACKGROUND OF THE INVENTION

Since the 1940's optical devices in the form of intraocular lenses (IOLs) have been utilized as replacements for diseased or damaged natural ocular lenses. In most cases, an intraocular lens is implanted within an eye at the time of surgically removing the diseased or damaged natural lens, such as for example, in the case of cataracts. For decades, the preferred material for fabricating such intraocular lenses was poly(methyl methacrylate), which is a rigid, glassy polymer.

Softer, more flexible IOLs have gained in popularity in recent years due to their ability to be compressed, folded, rolled or otherwise deformed. Such softer IOLs may be deformed prior to insertion thereof through an incision in the cornea of an eye. Following insertion of the IOL in an eye, the IOL returns to its original pre-deformed shape due to the memory characteristics of the soft material. Softer, more flexible IOLs as just described may be implanted into an eye through an incision that is much smaller, i.e., less than 4.0 mm, than that necessary for more rigid IOLs, i.e., 5.5 to 8.0 mm. A larger incision is necessary for more rigid IOLs because the lens must be inserted through an incision in the cornea slightly larger than the diameter of the inflexible IOL optic portion. Accordingly, more rigid IOLs have become less popular in the market since larger incisions have been found to be associated with an increased incidence of postoperative complications, such as induced astigmatism.

With recent advances in small-incision cataract surgery, increased emphasis has been placed on developing soft, foldable materials suitable for use in artificial IOLs. In general, these materials fall into one of three categories: hydrogels, silicones and low glass transition temperature acrylics.

In general, high water content hydrogel materials have relatively low refractive indexes, making them less desirable than other materials with respect to minimal incision size. Low refractive index materials require a thicker IOL optic portion to achieve a given refractive power. Silicone materials may have a higher refractive index than high-water content hydrogels, but tend to unfold explosively after being placed in the eye in a folded position. Explosive unfolding can potentially damage the corneal endothelium and/or rupture the natural lens capsule and associated zonules. Low glass transition temperature acrylic materials are desirable because they typically have a high refractive index and unfold more slowly and more controllably than silicone materials. Unfortunately, low glass transition temperature acrylic materials, which contain little or no water initially, may absorb pockets of water in vivo causing light reflections or "glistenings". Furthermore, it is difficult to achieve ideal folding and unfolding characteristics due to the temperature sensitivity of the acrylic polymers.

U.S. Pat. No. 5,480,950 issued Jan. 2, 1996 teaches of high refractive index hydrogel materials having a hydrated equilibrium water content of at least 57% for use in the manufacture of IOLs. The high refractive index hydrogel materials are cross-linked polymers prepared from mixtures of N-vinylpyrrolidone, 4-vinylpyrimidine and a vinyl pyridine having equilibrium water contents up to 90% and refractive indexes of 1.560 to 1.594 in the dry state. The IOLs as described are not implanted in a hydrated state. Rather, the IOLs are implanted in a dry, folded and elongated state and hydrated in situ. The refractive indexes in the hydrated state as used in the eye are not provided.

U.S. Pat. No. 5,693,095 issued Dec. 2, 1997 teaches of high refractive index, low water content IOL materials. The materials taught in this particular patent are acrylic materials having an elongation of at least 150%. IOLs manufactured from a material having such elongation characteristics will not crack, tear or split when folded. However, such low water content acrylic materials have been found to be less biocompatible than higher water content hydrogel materials when manufactured into and used as IOL devices.

SUMMARY OF THE INVENTION

Soft, foldable hydrogel lens materials having relatively high water contents and unexpectedly high refractive indexes particularly suited for use as intraocular lenses (IOLs), or other ophthalmic devices such as but not limited to contact lenses, keratoprostheses and corneal rings or inlays, have now been discovered. The subject hydrogel lens materials contain only two principal components: a high refractive index monomer that is usually hydrophobic but not necessarily so, and a hydrophilic monomer. The hydrogel materials of the present invention are copolymers comprising at least about 70% by weight of the two principal monomeric components whereby the hydrophilic monomer is present in an amount greater than that of the high refractive index monomer to maximize water content. The remainder of the hydrogel material formulation comprises up to approximately 30% water, cross-linkers, initiators, UV absorbers and like additives.

Accordingly, it is an object of the present invention to provide a biocompatible IOL material having a high refractive index.

Another object of the present invention is to provide a hydrogel IOL material having a high refractive index.

Another object of the present invention is to provide a hydrogel IOL material that has a high refractive index and is colorless.

Another object of the present invention is to provide a hydrogel IOL material that has a high refractive index and is transparent.

Still another object of the present invention is to provide a hydrogel IOL material that is relatively simple to manufacture.

These and other objectives and advantages of the present invention, some of which are specifically described and others that are not, will become apparent from the detailed description and claims that follow.

DETAILED DESCRIPTION OF THE INVENTION

The unique hydrogel materials of the present invention maximize both refractive index and water content for use in the manufacture of ophthalmic devices such as intraocular lenses (IOLs). Typical refractive indexes for acrylic polymers in the absence of water are on the order of 1.48 to 1.55, depending on the chemical structures of the monomer or comonomers comprising the material. Because the refractive index of water is low, i.e., 1.33, adding water to an acrylic polymer or copolymer decreases the refractive index of the hydrated material relative to the anhydrous polymer or copolymer. For this reason, the properties of refractive index and water content are inversely proportional. In the present invention, refractive index is maximized in the presence of water, by employing monomers that result in the highest refractive indexes in the absence of water. Monomers containing aryl groups, sulfur atoms or the halogens, chlorine, bromine and iodine form polymers having high refractive indexes. To maximize water content and refractive index in the present materials, a hydrophilic monomer is combined with a high refractive index comonomer. It is unexpected that such relatively high water content materials may be successfully synthesized to have high refractive indexes since water generally lowers the refractive indexes of hydrogels.

The presence of water in the materials of the present invention is desirable for two reasons, i.e., biocompatibility and flexibility. The presence of water usually renders a material more biocompatible than a corresponding material having no water content. Polymers containing some water are less prone to attach to living tissue. A water content of 25% or higher is most desirable to prevent the attachment and proliferation of lens epithelial cells on the IOL implant surface. Lower water content materials are acceptable for applications, such as phakic IOLs where the material will not be exposed to lens epithelial cells. Water also acts as an internal plasticizer, which makes the resulting material easier to fold or deform over a broad range of temperatures.

Materials of the present invention with high refractive indexes are also desirable to allow manufacturers to manufacture thinner IOLs. A thin IOL or thin IOL optic is critical in enabling a surgeon to minimize incision size. Keeping the surgical incision size to a minimum reduces intraoperative trauma and postoperative complications. A thin IOL is also critical for accommodating certain anatomical locations in the eye such as the anterior chamber and the ciliary sulcus. IOLs may be placed in the anterior chamber for increasing visual acuity in both aphakic and phakic eyes and placed in the ciliary sulcus for increasing visual acuity in phakic eyes.

The preferred hydrogel materials of the present invention have the flexibility required to allow the same to be folded or deformed so that IOLs made therefrom may be introduced into an eye through the smallest possible incision. To achieve this flexibility characteristic, the glass transition temperature (Tg) of the material is likewise of considerable importance. A glass transition temperature of 20 degrees Celsius or less measured by differential scanning calorimetry at 10 degrees Celsius per minute and determined at the midpoint of the transition of the heat flux curve, must be achieved in the subject materials to be acceptable for purposes of desirable folding of the implant. It was unexpected that materials could be synthesized having the desired refractive index, water content and glass transition temperature because many high refractive index monomers have bulky side-chains which restrict chain mobility and drastically increase the overall glass transition temperature of the copolymer. As a general rule, acrylates produce polymers with lower glass transition temperatures than the corresponding methacrylates and are therefor preferred. As mentioned above, the water content of the subject materials also plays an important role in the foldability and deformability of the subject material. Polymer flexibility was found to be proportional to water content and polymer glass transition temperature and refractive index were found to be inversely proportional to water content. Therefore, a delicate balance between water content, glass transition temperature and refractive index must be struck in the synthesis of the subject unique hydrogel materials to be suitable for use in ophthalmic applications.

The novel hydrogel materials of the present invention are copolymers comprising only two principal monomeric components: a high refractive index monomer and a hydrophilic monomer. The unique characteristics of the materials of the present invention are achieved using a larger amount of the hydrophilic monomer than that of the high refractive index monomer. Accordingly, it is unexpected that the relatively high water content hydrogel materials of the present invention would have the high refractive indexes achieved since water generally lowers the refractive index thereof.

Hydrophilic monomers suitable for use in the manufacture of the materials of the present invention are represented by Formula I below Formula I

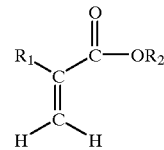

wherein $R_1$ is selected from the group consisting of hydrogen and $C_{1-6}$ alkyl such as for example but not limited to methyl, ethyl, propyl and butyl but preferably methyl for its common availability, and $R_2$ is selected from the group consisting of hydrogen, an alkali metal or an alkaline earth metal such as for example but not limited to sodium, potassium and magnesium, $C_{1-6}$ hydroxyalkyl such as for example but not limited to hydroxyethyl, hydroxypropyl and hydroxybutyl, $C_{4-12}$ hydroxyalkoxyalkyl such as for example but not limited to hydroxyethoxyethyl, hydroxybutoxybutyl and hydroxymethoxypropyl, $C_{4-12}$ hydroxydialkoxyalkyl such as for example but not limited to hydroxydiethoxyethyl, hydroxydibutoxybutyl and hydroxydiethoxypropyl, $C_{2-12}$ alkoxyalkyl such as for example but not limited to methoxyethyl and ethoxybutyl, $C_{3-12}$ polyalkoxyalkyl such as for example but not limited to methoxyethoxyethyl, methoxyethoxybutyl, and ethoxybutoxyethyl, $C_{3-15}$ polyalkoxyhydroxyalkyl such as for example but not limited to polyethylene glycol, polypropylene glycol and polybutylene glycol, and $C_{2-12}$ dihydroxyalkyl such as for example but not limited to glycerol, dihydroxybutyl and dihydroxyhexyl.

Suitable hydrophilic monomers for use in the present invention include for example but are not limited to 2-hydroxyethyl methacrylate, hydroxyethoxyethyl methacrylate, hydroxydiethoxyethyl methacrylate, methoxyethyl methacrylate, methoxyethoxyethyl methacrylate, methoxydiethoxyethyl methacrylate, poly(ethylene glycol) methacrylate, methoxy-poly(ethylene glycol) methacrylate, methacrylic acid, sodium methacrylate, glycerol methacrylate, hydroxypropyl methacrylate, and hydroxybutyl methacrylate.

The preferred hydrophilic monomer is 2-hydroxyethyl methacrylate (HEMA) to maximize water content.

High refractive index monomers suitable for use in the manufacture of the materials of the present invention are represented by Formulas II through IV below,

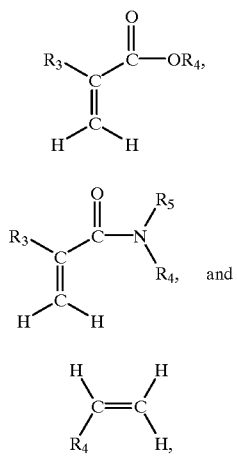

Formula II

Formula III

Formula IV wherein $R_3$ is selected from the group consisting of hydrogen and $C_{1-4}$ alkyl such as for example but not limited to methyl, ethyl and propyl but preferably hydrogen and methyl for common availability, $R_4$ is selected from the group consisting of $C_{6-25}$ aryl such as for example but not limited to phenyl and diphenyl, $C_{6-25}$ hydroxyaryl such as for example but not limited to hydroxyphenyl and hydroxydiphenyl, $C_{6-25}$ aryloxyaryl such as for example but not limited to phenoxyphenyl and diphenoxyphenyl, $C_{12-25}$ polyhydroxyaryl such as for example but not limited to polyhydroxyphenyl and polyhydroxydiphenyl, $C_{12-35}$ polyaryl such as for example but not limited to diphenyl and triphenyl, $C_{6-15}$ arylalkyl such as for example but not limited to benzyl, 2-phenylethyl and 3-phenylpropyl, $C_{12-35}$ polyarylalkyl such as for example but not limited to diphenylmethyl, diphenylethyl, diphenylpropyl and triphenylmethyl, $C_{6-15}$ alkoxyaryl such as for example but not limited to 4-methoxybenzyl, 4-ethoxybenzyl and 4-butoxybenzyl, $C_{6-15}$ aryl halides such as for example but not limited to pentabromophenyl, pentachlorophenyl and tribromophenyl, $C_{6-15}$ aryloxyalkyl such as for example but not limited to 2-phenoxyethyl, 3-phenoxypropyl and 4-phenoxybutyl, $C_{1-7}$ alkyl halides such as for example but not limited to 2,3-dibromopropyl, 2,3-dichloropropyl and 2,3-dibromobutyl, $C_{6-15}$ arylthioalkyl such as for example but not limited to phenylthioethyl, phenylthiopropyl and phenylthiobutyl, $C_{6-15}$ aryloxyalkyl halides such as for example but not limited to 4-chlorophenoxyethyl, 4-bromophenoxyethyl and 3,5-dichlorophenoxyethyl and $C_{6-15}$ aryloxyalkoxyalkyl such as for example but not limited to 2-phenoxyethoxyethyl and 2-phenoxyethoxybutyl, and $R_5$ is selected from the group consisting of hydrogen, $C_{1-3}$ alkyl such as for example but not limited to methyl and propyl, and $C_{6-15}$ alkylaryl such as for example but not limited to methylphenyl, propylphenyl and butylphenyl.

Suitable high refractive index monomers include for example but are not limited to phenyl acrylate, phenyl methacrylate, benzyl acrylate, benzyl methacrylate, 2-phenylethyl acrylate, 2-phenylethyl methacrylate, 2-phenoxyethyl acrylate, 2-phenoxyethyl methacrylate, phenylthioethyl acrylate, phenylthioethyl methacrylate, 2,4,6-tribromophenyl acrylate, 2,4,6-tribromophenyl methacrylate, pentabromophenyl acrylate, pentabromophenyl methacrylate, pentachlorophenyl acrylate, pentachlorophenyl methacrylate, 2,3-dibromopropyl acrylate, 2,3-dibromopropyl methacrylate, 2-naphthyl acrylate, 2-naphthyl methacrylate, 4-methoxybenzyl acrylate, 4-methoxybenzyl methacrylate, 2-benzyloxyethyl acrylate, 2-benzyloxyethyl methacrylate, 4-chlorophenoxyethyl acrylate, 4-chlorophenoxyethyl methacrylate, 2-phenoxyethoxyethyl acrylate, 2-phenoxyethoxyethyl methacrylate, N-phenyl acrylamide, N-phenyl methacrylamide, N-benzyl acrylamide, N-benzyl methacrylamide, N,N-dibenzyl acrylamide, N,N-dibenzyl methacrylamide, N-diphenylmethyl acrylamide, N-(4-methylphenyl)methyl acrylamide, N-1-naphthyl acrylamide, N-4-nitrophenyl acrylamide, N-2-phenylethyl) acrylamide, N-triphenylmethyl acrylamide, N-(4-hydroxyphenyl) acrylamide, N,N-methylphenyl acrylamide, N,N-phenyl phenylethyl acrylamide, N-diphenylmethyl methacrylamide, N-(4-methyl phenyl)methyl methacrylamide, N-1-naphthyl methacrylamide, N-4-nitrophenyl methacrylamide, N-2-phenylethyl) methacrylamide, N-triphenylmethyl methacrylamide, N-(4-hydroxyphenyl) methacrylamide, N,N-methylphenyl methacrylamide, N,N'-phenyl phenylethyl methacrylamide, N-vinylcarbazole, 4-vinylpyridine, 2-vinylpyridine, styrene, 2-chlorostyrene, 3-chlorostyrene, 4-chlorostyrene, 2-bromostyrene, 3-bromostyrene, 4-bromostyrene, 2,6-dichlorostyrene, 2-iodostyrene, 3-iodostyrene, 4-iodostyrene, pentabromostyrene, 4-phenylstyrene, 1-vinylnaphthalene, 2-vinylnaphthalene, 9-vinylanthracene and 4-phenoxystyrene.

Preferred high refractive index monomers for use in the present invention include phenyl methacrylate, benzyl acrylate, benzyl methacrylate, 2-phenylethyl acrylate, 2-phenylethyl methacrylate, 2-phenoxyethyl acrylate, 2-phenoxyethyl methacrylate, 2,3-dibromopropyl acrylate, N-benzyl methacrylamide, N-vinylcarbazole, 2-phenylthioethyl acrylate and 2-phenylthioethyl methacrylate to achieve the unexpectedly high refractive index hydrogel materials of the present invention which are both flexible and biocompatible.

The materials of the present invention are copolymers comprising a total of at least approximately 70 but more preferably approximately 70 to 90 but most preferably approximately 75 percent by weight of the two principal components described above whereby the hydrophilic monomer is present in an amount greater than that of the high refractive index monomer to maximize water content.

Hydrogel compositions of the present invention include for example but are not limited to poly(2-hydroxyethyl methacrylate-co-phenyl acrylate), poly(2-hydroxyethyl methacrylate-co-phenyl methacrylate), poly(2-hydroxyethyl methacrylate-co-benzyl acrylate), poly(2-hydroxyethyl methacrylate-co-benzyl methacrylate), poly(2-hydroxyethyl methacrylate-co-2-phenylethyl acrylate), poly(2-hydroxyethyl methacrylate-co-2-phenylethyl methacrylate), poly(2-hydroxyethyl methacrylate-co-2-phenoxyethyl acrylate), poly(2-hydroxyethyl methacrylate-co-2-phenoxyethyl methacrylate), poly(2-hydroxyethyl methacrylate-co-phenylthioethyl acrylate), poly(2-hydroxyethyl methacrylate-co-phenylthioethyl methacrylate), poly(2-hydroxyethyl methacrylate-co-2,4,6-tribromophenyl acrylate), poly(2-hydroxyethyl methacrylate-co-2,4,6-tribromophenyl methacrylate), poly(2-hydroxyethyl methacrylate-co-pentabromophenyl acrylate), poly(2-hydroxyethyl methacrylate-co-pentabromophenyl methacrylate), poly(2-hydroxyethyl methacrylate-co-pentachlorophenyl acrylate), poly(2-hydroxyethyl methacrylate-co-pentachlorophenyl methacrylate), poly(2-hydroxyethyl methacrylate-co-2,3-dibromopropyl acrylate), poly(2-hydroxyethyl methacrylate-co-2,3-dibromopropyl methacrylate), poly(2-hydroxyethyl methacrylate-co-2-naphthyl acrylate), poly(2-hydroxyethyl methacrylate-co-2-naphthyl methacrylate), poly(2-hydroxyethyl methacrylate-co-4-methoxybenzyl acrylate), poly(2-hydroxyethyl methacrylate-co-4-methoxybenzyl methacrylate), poly(2-hydroxyethyl methacrylate-co-2-benzyloxyethyl acrylate), poly(2-hydroxyethyl methacrylate-co-4-chlorophenoxyethyl acrylate), poly(2-hydroxyethyl methacrylate-co-2-phenoxyethoxyethyl acrylate), poly(2-hydroxyethyl methacrylate-co-2-benzyloxyethyl methacrylate), poly(2-hydroxyethyl methacrylate-co-4-chlorophenoxyethyl methacrylate), poly(2-hydroxyethyl methacrylate-co-2-phenoxyethoxyethyl methacrylate), poly(2-hydroxyethyl methacrylate-co-N-phenyl acrylamide), poly(2-hydroxyethyl methacrylate-co-N-phenyl methacrylamide), poly(2-hydroxyethyl methacrylate-co-N-benzyl acrylamide), poly(2-hydroxyethyl methacrylate-co-N-benzyl methacrylamide), poly(2-hydroxyethyl methacrylate-co-N,N-dibenzyl acrylamide), poly(2-hydroxyethyl methacrylate-co-N,N-dibenzyl methacrylamide), poly(2-hydroxyethyl methacrylate-co-N-diphenylmethyl acrylamide), poly(2-hydroxyethyl methacrylate-co-N-(4-methyl phenyl)methyl acrylamide), poly(2-hydroxyethyl methacrylate-co-N-1-naphthyl acrylamide), poly(2-hydroxyethyl methacrylate-co-N-4-nitrophenyl acrylamide), poly(2-hydroxyethyl methacrylate-co-2-phenylethyl acrylamide), poly(2-hydroxyethyl methacrylate-co-N-triphenylmethyl acrylamide), poly(2-hydroxyethyl methacrylate-co-N-(4-hydroxyphenyl) acrylamide), poly(2-hydroxyethyl methacrylate-co-N,N-methyl phenyl acrylamide), poly(2-hydroxyethyl methacrylate-co-N,N-phenyl phenylethyl acrylamide), poly(2-hydroxyethyl methacrylate-co-N-diphenylmethyl methacrylamide), poly(2-hydroxyethyl methacrylate-co-N-(4-methyl phenyl)methyl methacrylamide), poly(2-hydroxyethyl methacrylate-co-N-1-naphthyl methacrylamide), poly(2-hydroxyethyl methacrylate-co-N-4-nitrophenyl methacrylamide), poly(2-hydroxyethyl methacrylate-co-2-phenylethyl methacrylamide), poly(2-hydroxyethyl methacrylate-co-N-triphenylmethyl methacrylamide), poly(2-hydroxyethyl methacrylate-co-N-(4-hydroxyphenyl) methacrylamide), poly(2-hydroxyethyl methacrylate-co-N,N-methyl phenyl methacrylamide), poly(2-hydroxyethyl methacrylate-co-N,N-phenyl phenylethyl methacrylamide), poly(2-hydroxyethyl methacrylate-co-N-vinylcarbazole), poly(2-hydroxyethyl methacrylate-co-4-vinylpyridine), poly(2-hydroxyethyl methacrylate-co-2-vinylpyridine), poly(2-hydroxyethyl methacrylate-co-styrene), poly(2-hydroxyethyl methacrylate-co-2-chlorostyrene), poly(2-hydroxyethyl methacrylate-co-3-chlorostyrene), poly(2-hydroxyethyl methacrylate-co-4-chlorostyrene), poly(2-hydroxyethyl methacrylate-co-2-bromostyrene), poly(2-hydroxyethyl methacrylate-co-3-bromostyrene), poly(2-hydroxyethyl methacrylate-co-4-bromostyrene), poly(2-hydroxyethyl methacrylate-co-2,6-dichlorostyrene), poly(2-hydroxyethyl methacrylate-co-2-iodostyrene), poly(2-hydroxyethyl methacrylate-co-3-iodostyrene), poly(2-hydroxyethyl methacrylate-co-4-iodostyrene), poly(2-hydroxyethyl methacrylate-co-pentabromostyrene), poly(2-hydroxyethyl methacrylate-co-4-phenylstyrene), poly(2-hydroxyethyl methacrylate-co-1-vinylnaphthalene), poly(2-hydroxyethyl methacrylate-co-2-vinylnaphthalene), poly(2-hydroxyethyl methacrylate-co-9-vinylanthracene), poly(2-hydroxyethyl methacrylate-co-4-phenoxystyrene), poly(hydroxyethoxyethyl methacrylate-co-phenyl methacrylate), poly(hydroxyethoxyethyl methacrylate-co-benzyl acrylate), poly(hydroxyethoxyethyl methacrylate-co-benzyl methacrylate), poly(hydroxyethoxyethyl methacrylate-co-2-phenylethyl acrylate), poly(hydroxyethoxyethyl methacrylate-co-2-phenylethyl methacrylate), poly(hydroxyethoxyethyl methacrylate-co-2-phenoxyethyl acrylate), poly(hydroxyethoxyethyl methacrylate-co-2-phenoxyethyl methacrylate), poly(hydroxyethoxyethyl methacrylate-co-2,3-dibromopropyl acrylate), poly(hydroxyethoxyethyl methacrylate-co-N-benzyl methacrylamide), poly(hydroxyethoxyethyl methacrylate-co-N-vinylcarbazole), poly(hydroxyethoxyethyl methacrylate-co-2-phenylthioethyl methacrylate), poly(hydroxyethoxyethyl methacrylate-co-2-phenylthioethyl acrylate), poly(hydroxydiethoxyethyl methacrylate-co-phenyl methacrylate), poly(hydroxydiethoxyethyl methacrylate-co-benzyl acrylate), poly(hydroxydiethoxyethyl methacrylate-co-benzyl methacrylate), poly(hydroxydiethoxyethyl methacrylate-co-2-phenylethyl acrylate), poly(hydroxydiethoxyethyl methacrylate-co-2-phenylethyl methacrylate), poly(hydroxydiethoxyethyl methacrylate-co-2-phenoxyethyl acrylate), poly(hydroxydiethoxyethyl methacrylate-co-2-phenoxyethyl methacrylate), poly(hydroxydiethoxyethyl methacrylate-co-2,3-dibromopropyl acrylate), poly(hydroxydiethoxyethyl methacrylate-co-N-benzyl methacrylamide), poly(hydroxydiethoxyethyl methacrylate-co-N-vinylcarbazole), poly(hydroxydiethoxyethyl methacrylate-co-2-phenylthioethyl acrylate), poly(hydroxydiethoxyethyl methacrylate-co-phenylthioethyl methacrylate), poly(methoxyethyl methacrylate-co-phenyl methacrylate), poly(methoxyethyl methacrylate-co-benzyl acrylate), poly(methoxyethyl methacrylate-co-benzyl methacrylate), poly(methoxyethyl methacrylate-co-2-phenylethyl acrylate), poly(methoxyethyl methacrylate-co-2-phenylethyl methacrylate), poly(methoxyethyl methacrylate-co-2-phenoxyethyl acrylate), poly(methoxyethyl methacrylate-co-2-phenoxyethyl methacrylate), poly(methoxyethyl methacrylate-co-2,3-dibromopropyl acrylate), poly(methoxyethyl methacrylate-co-N-benzyl methacrylamide), poly(methoxyethyl methacrylate-co-N-vinylcarbazole), poly(methoxyethyl methacrylate-co-2-phenylthioethyl acrylate), poly(methoxyethyl methacrylate-co-2-phenylthioethyl methacrylate), poly(methoxyethoxyethyl methacrylate-co-phenyl methacrylate), poly(methoxyethoxyethyl methacrylate-co-benzyl acrylate), poly(methoxyethoxyethyl methacrylate-co-benzyl methacrylate), poly(methoxyethoxyethyl methacrylate-co-2-phenylethyl acrylate), poly(methoxyethoxyethyl methacrylate-co-2-phenylethyl methacrylate), poly(methoxyethoxyethyl methacrylate-co-2-phenoxyethyl acrylate), poly(methoxyethoxyethyl methacrylate-co-2-phenoxyethyl methacrylate), poly(methoxyethoxyethyl methacrylate-co-2,3-dibromopropyl acrylate), poly(methoxyethoxyethyl methacrylate-co-N-benzyl methacrylamide), poly(methoxyethoxyethyl methacrylate-co-N-vinylcarbazole), poly(methoxyethoxyethyl methacrylate-co-2-phenylthioethyl acrylate), poly(methoxyethoxyethyl methacrylate-co-2-phenylthioethyl methacrylate), poly(methoxydiethoxyethyl methacrylate-co-phenyl methacrylate), poly(methoxydiethoxyethyl methacrylate-co-benzyl acrylate), poly(methoxydiethoxyethyl methacrylate-co-benzyl methacrylate), poly(methoxydiethoxyethyl methacrylate-co-2-phenylethyl acrylate), poly(methoxydiethoxyethyl methacrylate-co-2-phenylethyl methacrylate), poly(methoxydiethoxyethyl methacrylate-co-2-phenoxyethyl acrylate), poly(methoxydiethoxyethyl methacrylate-co-2-phenoxyethyl methacrylate), poly(methoxydiethoxyethyl methacrylate-co-2,3-dibromopropyl acrylate), poly(methoxydiethoxyethyl methacrylate-co-N-benzyl methacrylamide), poly(methoxydiethoxyethyl methacrylate-co-N-vinylcarbazole), poly(methoxydiethoxyethyl methacrylate-co-2-phenylthioethyl acrylate), poly(methoxydiethoxyethyl methacrylate-co-2-phenylthioethyl methacrylate), poly(poly(ethylene glycol) methacrylate-co-phenyl methacrylate), poly(poly(ethylene glycol) methacrylate-co-benzyl acrylate), poly(poly(ethylene glycol) methacrylate-co-benzyl methacrylate), poly(poly(ethylene glycol) methacrylate-co-2-phenylethyl acrylate), poly(poly(ethylene glycol) methacrylate-co-2-phenylethyl methacrylate), poly(poly(ethylene glycol) methacrylate-co-2-phenoxyethyl acrylate), poly(poly(ethylene glycol) methacrylate-co-2-phenoxyethyl methacrylate), poly(poly(ethylene glycol) methacrylate-co-2,3-dibromopropyl acrylate), poly(poly(ethylene glycol) methacrylate-co-N-benzyl methacrylamide), poly(poly(ethylene glycol) methacrylate-co-N-vinylcarbazole), poly(poly(ethylene glycol) methacrylate-co-2-phenylthioethyl acrylate), poly(poly(ethylene glycol) methacrylate-co-2-phenylthioethyl methacrylate), poly(methoxy-poly(ethylene glycol) methacrylate-co-phenyl methacrylate), poly(methoxy-poly(ethylene glycol) methacrylate-co-benzyl acrylate), poly(methoxy-poly(ethylene glycol) methacrylate-co-benzyl methacrylate), poly(methoxy-poly(ethylene glycol) methacrylate-co-2-phenylethyl acrylate), poly(methoxy-poly(ethylene glycol) methacrylate-co-2-phenylethyl methacrylate), poly(methoxy-poly(ethylene glycol) methacrylate-co-2-phenoxyethyl acrylate), poly(methoxy-poly(ethylene glycol) methacrylate-co-2-phenoxyethyl methacrylate), poly(methoxy-poly(ethylene glycol) methacrylate-co-2,3-dibromopropyl acrylate), poly(methoxy-poly(ethylene glycol) methacrylate-co-N-benzyl methacrylamide), poly(methoxy-poly(ethylene glycol) methacrylate-co-N-vinylcarbazole), poly(methoxy-poly(ethylene glycol) methacrylate-co-2-phenylthioethyl acrylate), poly(methoxy-poly(ethylene glycol) methacrylate-co-2-phenylthioethyl methacrylate), poly(methacrylic acid-co-phenyl methacrylate), poly(methacrylic acid-co-benzyl acrylate), poly(methacrylic acid-co-benzyl methacrylate), poly(methacrylic acid-co-2-phenylethyl acrylate), poly(methacrylic acid-co-2-phenylethyl methacrylate), poly(methacrylic acid-co-2-phenoxyethyl acrylate), poly(methacrylic acid-co-2-phenoxyethyl methacrylate), poly(methacrylic acid-co-2,3-dibromopropyl acrylate), poly(methacrylic acid-co-N-benzyl methacrylamide), poly(methacrylic acid-co-N-vinylcarbazole), poly(methacrylic acid-co-2-phenylthioethyl acrylate), poly(methacrylic acid-co-2-phenylthioethyl methacrylate), poly(sodium methacrylate-co-phenyl methacrylate), poly(sodium methacrylate-co-benzyl acrylate), poly(sodium methacrylate-co-benzyl methacrylate), poly(sodium methacrylate-co-2-phenylethyl acrylate), poly(sodium methacrylate-co-2-phenylethyl methacrylate), poly(sodium methacrylate-co-2-phenoxyethyl acrylate), poly(sodium methacrylate-co-2-phenoxyethyl methacrylate), poly(sodium methacrylate-co-2,3-dibromopropyl acrylate), poly(sodium methacrylate-co-N-benzyl methacrylamide), poly(sodium methacrylate-co-N-vinylcarbazole), poly(sodium methacrylate-co-2-phenylthioethyl acrylate), poly(sodium methacrylate-co-2-phenylthioethyl methacrylate), poly(glycerol methacrylate-co-phenyl methacrylate), poly(glycerol methacrylate-co-benzyl acrylate), poly(glycerol methacrylate-co-benzyl methacrylate), poly(glycerol methacrylate-co-2-phenylethyl acrylate), poly(glycerol methacrylate-co-2-phenylethyl methacrylate), poly(glycerol methacrylate-co-2-phenoxyethyl acrylate), poly(glycerol methacrylate-co-2-phenoxyethyl methacrylate), poly(glycerol methacrylate-co-2,3-dibromopropyl acrylate), poly(glycerol methacrylate-co-N-benzyl methacrylamide), poly(glycerol methacrylate-co-N-vinylcarbazole), poly(glycerol methacrylate-co-2-phenylthioethyl acrylate), poly(glycerol methacrylate-co-2-phenylthioethyl methacrylate), poly(hydroxypropyl methacrylate-co-phenyl methacrylate), poly(hydroxypropyl methacrylate-co-benzyl acrylate), poly(hydroxypropyl methacrylate-co-benzyl methacrylate), poly(hydroxypropyl methacrylate-co-2-phenylethyl acrylate), poly(hydroxypropyl methacrylate-co-2-phenylethyl methacrylate), poly(hydroxypropyl methacrylate-co-2-phenoxyethyl acrylate), poly(hydroxypropyl methacrylate-co-2-phenoxyethyl methacrylate), poly(hydroxypropyl methacrylate-co-2,3-dibromopropyl acrylate), poly(hydroxypropyl methacrylate-co-N-benzyl methacrylamide), poly(hydroxypropyl methacrylate-co-N-vinylcarbazole), poly(hydroxypropyl methacrylate-co-2-phenylthioethyl acrylate), poly(hydroxypropyl methacrylate-co-2-phenylthioethyl methacrylate), poly(hydroxybutyl methacrylate-co-phenyl methacrylate), poly(hydroxybutyl methacrylate-co-benzyl acrylate), poly(hydroxybutyl methacrylate-co-benzyl methacrylate), poly(hydroxybutyl methacrylate-co-2-phenylethyl acrylate), poly(hydroxybutyl methacrylate-co-2-phenylethyl methacrylate), poly(hydroxybutyl methacrylate-co-2-phenoxyethyl acrylate), poly(hydroxybutyl methacrylate-co-2-phenoxyethyl methacrylate), poly(hydroxybutyl methacrylate-co-2,3-dibromopropyl acrylate), poly(hydroxybutyl methacrylate-co-N-benzyl methacrylamide), poly(hydroxybutyl methacrylate-co-N-vinylcarbazole), poly(hydroxybutyl methacrylate-co-2-phenylthioethyl acrylate) and poly(hydroxybutyl methacrylate-co-2-phenylthioethyl methacrylate).

Preferred hydrogel compositions of the present invention include poly(2-hydroxyethyl methacrylate-co-phenyl methacrylate), poly(2-hydroxyethyl methacrylate-co-benzyl acrylate), poly(2-hydroxyethyl methacrylate-co-benzyl methacrylate), poly(2-hydroxyethyl methacrylate-co-2-phenylethyl acrylate), poly(2-hydroxyethyl methacrylate-co-2-phenylethyl methacrylate), poly(2-hydroxyethyl methacrylate-co-2-phenoxyethyl acrylate), poly(2-hydroxyethyl methacrylate-co-2-phenoxyethyl methacrylate), poly(2-hydroxyethyl methacrylate-co-N-benzyl methacrylamide) and poly(2-hydroxyethyl methacrylate-co-N-vinylcarbazole) to achieve the unexpectedly high refractive index hydrogel materials of the present invention which are both flexible and biocompatible.

The subject hydrogel materials are synthesized by polymerizing one or more of the above-described hydrophilic monomers with one or more high refractive index monomers, most preferably having phenyl, sulfur or halogen moieties, in the presence of at least 0.01 but more preferably 0.01 to 2.0 mole percent crosslinker, at least 0.02 but more preferably 0.02 to 2.0 weight percent initiator and optionally at least 0.1 but more preferably 0.1 to 2.0 weight percent ultraviolet light absorber.

Suitable crosslinkers include for example but are not limited to ethylene glycol dimethacrylate, diethylene glycol dimethacrylate, triethylene glycol dimethacrylate and poly(ethylene glycol) dimethacrylate wherein ethylene glycol dimethacrylate is preferred. Suitable initiators include for example but are not limited to azobis(isobutyronitrile), 2,2'-azobis(2,4-dimethylvaleronitrile), 2,2'-azobis (methylbutyronitrile), 1,1'-azobis(cyanocyclohexane), di-t-butyl peroxide, dicumyl peroxide, t-butylcumyl peroxide, 2,5-dimethyl-2,5-bis(2-ethylhexanoyl peroxy)hexane, t-butyl peroxyneodecanote, t-butyl peroxy 2-ethylhexanoate, di(4-t-butyl cyclohexyl) peroxydicarbonate, t-butyl peroxypivalate, decanoyl peroxide, lauroyl peroxide, benzoyl peroxide, 2,4-pentanedione peroxide, di(n-propyl) peroxydicarbonate, t-amyl peroxyneodecanoate and t-butyl peroxyacetate wherein 2,2'-azobis(isobutyronitrile) is preferred. Suitable ultraviolet light absorbers include for example but are not limited to beta-(4-benzotriazoyl-3-hydroxyphenoxy)ethyl acrylate, 4-(2-acryloxyethoxy)-2-hydroxybenzophenone, 4-methacryloxy-2-hydroxybenzophenone, 2-(2'-methacryloxy-5'-methylphenyl)benzotriazole, 2-(2'-hydroxy-5'-methacryoxyethylphenyl)-2H-benzotriazole, 2-[3'-tert-Butyl-2'-hydroxy-5'-(3"-methacryloyloxypropyl) phenyl]-5-chlorobenzotriazole, 2-(3'-tert-Butyl-5'-(3"-dimethylvinylsilylpropoxy)-2'-hydroxyphenyl]-5-methoxybenzotriazole, 2-(3'-Allyl-2'-hydroxy-5'-methylphenyl)benzotriazole, 2-[3'-tert-Butyl-2'-hydroxy-5'-(3"methacryloyloxypropoxy)phenyl]-5-methoxybenzotriazole, and 2-[3'-tert-Butyl-2'-hydroxy-5'-(3"-methacryloyloxypropoxy)phenyl]-5-chlorobenzotriazole wherein beta-(4-benzotriazolyl-3-hydroxyphenoxy)ethyl acrylate is the preferred ultraviolet light absorber.

The subject hydrogel materials having a refractive index of approximately 1.45 or greater and approximately 5 to 30 percent water by weight measured by an Abbe refractometer at 589 nm and 37 degrees Celsius with a sodium light source are described in still greater detail in the examples that follow.

EXAMPLES

Example 1

Monomers and Purification Thereof

HEMA of low acid, low inhibitor (LALI) grade was obtained from Benz Research and Development, Sarasota, Fla. and was used without further purification. Phenyl-containing acrylates and methacrylates were obtained and purified as indicated below.

| Monomer | Source | Purification |
|---|---|---|
| 2-phenoxyethyl methacrylate (POEMA) | Sartomer West Chester, PA | None |
| 2-phenylethyl methacrylate (PEMA) | Polysciences Warrington, PA | None |
| 2-phenoxyethyl acrylate (POEA) | Polysciences Warrington, PA | Percolation through neutral alumina |
| 2-phenylethyl acrylate (PEA) | Polysciences Warrington, PA | Percolation through basic alumina |

Ethylene glycol dimethacrylate (EGDMA, Sartomer, West Chester, Pa.) crosslinker was extracted with aqueous NaOH and distilled from $CuCl_2$ prior to use and azobis (isobutyronitrile) (AIBN) initiator was used as received from Polysciences.

Example 2

Polymer Synthesis

HEMA and each comonomer were combined in flasks in the following mole ratios.

| Mol HEMA/Mol Comonomer |
|---|
| 90/10 |
| 85/15 |
| 80/20 |
| 75/25 |
| 70/30 |
| 65/35 |
| 60/40 |

Enough EGDMA crosslinker was added to comprise 0.25 mole percent of total moles of HEMA and comonomer. The amount of AIBN initiator added to each solution was 0.05 to 0.1 weight percent of the total weight of monomers.

The unfiltered solutions were poured into polypropylene culture tubes (16×125 mm, Fisher Scientific), capped, and placed in a 60 degree Celsius water bath for approximately 22 to 26 hours but most preferably 24 hours. Post-cure was effected for approximately 22 to 26 hours but most preferably 24 hours in a forced-air oven maintained at 120 degrees Celsius. The resultant polymer rods were demolded and sliced into 3.0 mm thick disks with a tool-room lathe. Five sample disks of each composition were lathed to 2.0 mm thickness with a diamond-turning lathe.

Example 3

Polymer Characterizations

The initial masses of the disks prepared as described above were determined to 0.0001 g on an analytical balance. The disks were placed into scintillation vials with 20 mL of balanced salt solution (BSS) Cytosol, Braintree, Mass., and hydrated in a constant temperature bath maintained at 37 degrees Celsius, Lauda, Model RM 20, Brinkmann Instruments, Inc., Westbury, N.Y. The masses of the disks were checked periodically by blotting dry with a Kimwipe™, Kimberly-Clarke, Roswell, Ga., and weighing to 0.0001 g. After achieving constant mass, the refractive index of each specimen was determined on an Abbey™ refractometer, Reichert-Jung, Model 10480, Reichert Scientific Instruments, Buffalo, N.Y., maintained at 37 degrees Celsius. The samples were then dried in a forced-air oven at 120 degrees Celsius for approximately 18 to 30 hours, but more preferably 24 hours and reweighed to 0.001 g.

The equilibrium water content (EWC) for each disk was determined using the following equation.

$$EWC, \% = \frac{\text{Mass (hydrated)} - \text{Mass (dehydrated)}}{\text{Mass (hydrated)}} \times 100$$

The average refractive index and standard deviation were calculated for each composition. The Shore D hardness of non-hydrated HEMA/POEA copolymer compositions was determined at room temperature with a hand-held durometer. The average hardness and standard deviation was determined from ten measurements of each composition.

Example 4

Polymer Study Results

Three of the four groups of polymers had good optical clarity. HEMA/PEA polymers had a considerable amount of haze, yet the refractive index could be determined. HEMA/POEA and HEMA/PEA polymer series were flexible and foldable at all formulations studied. Flexibility increased slightly with increasing water content. HEMA/POEMA and HEMA/PEMA polymers were flexible and foldable only in the cases of the highest water-containing compositions.

All specimens were machined at room temperature. Harder specimens, i.e., those with the highest HEMA content, were most easily lathe-cut. The Shore D hardness of the HEMA/POEA series of polymers demonstrated that xerogel hardness decreased with increasing levels of POEA as set forth in Table 1 below. Both HEMA/methacrylate polymer series remained hard with increasing methacrylate content.

TABLE 1

Shore D Hardness of HEMA/POEA Xerogel Compositions

| HEMA/POEA | Shore D Hardness +/- std. Dev. |
|---|---|
| 90/10 | 84 +/- 2 |
| 85/15 | 83 +/- 1 |
| 80/20 | 83 +/- 2 |
| 75/25 | 81 +/- 1 |
| 70/30 | 78 +/- 2 |
| 65/35 | 76 +/- 2 |
| 60/40 | 74 +/- 2 |

Equilibrium water content and refractive index results are presented in Tables 2 and 3 below. For a given mass of HEMA and comonomer, the methacrylate monomers imparted higher hydrated refractive indexes than did the acrylate monomers. The order of refractive index-enhancing effectiveness of the phenyl monomer was as follows.

PEMA>POEMA>PEA>POEA

The refractive index of each composition was more dependent upon water content than phenyl-containing comonomer. However, per given mass of HEMA and comonomer, the acrylic compositions contained more water than the methacrylate compositions. Accordingly, hydrogels with refractive indexes above 1.5 are obtainable by copolymerizing HEMA with phenyl-containing acrylic monomers.

TABLE 2

Equilibrium Water Content (EWC) Results For HEMA Copolymers

| Mole Ratio HEMA/ comonomer (mol/mol) | COMONOMER | | | | |
|---|---|---|---|---|---|
| | POEM EWC, % +/- std. dev. | PEM EWC, % +/- std. dev. | POEA EWC, % +/- std. dev. | PEA EWC, % +/- std. dev. | |
| 90/10 | 22.42 +/- .01 | 22.75 +/- .04 | 24.43 +/- .05 | 24.79 +/- .01 | |
| 85/15 | 18.21 +/- .02 | 18.51 +/- .03 | 20.67 +/- .04 | 21.08 +/- .03 | |
| 80/20 | 15.11 +/- .03 | 15.42 +/- .15 | 17.70 +/- .02 | 18.04 +/- .02 | |
| 75/25 | 12.74 +/- .07 | 12.80 +/- .09 | 15.19 +/- .06 | 15.55 +/- .02 | |
| 70/30 | 10.90 +/- .21 | 10.63 +/- .10 | 13.21 +/- .03 | 13.30 +/- .03 | |
| 65/35 | 9.53 +/- .19 | 9.05 +/- .20 | 11.45 +/- .04 | 11.45 +/- .03 | |
| 60/40 | 8.39 +/- .08 | 7.58 +/- .04 | 9.97 +/- .06 | 9.73 +/- .02 | |

TABLE 2-continued

Equilibrium Water Content (EWC) Results For HEMA Copolymers

| Mole Ratio HEMA/ comonomer (mol/mol) | COMONOMER | | | | |
|---|---|---|---|---|---|
| | DBPA* EWC, % | BA** EWC, % | BMA*** EWC, % | PMA**** EWC, % | BMAAM***** EWC, % |
| 95/5 | 30.0 | 29.1 | 28.8 | 28.8 | 31.5 |
| 90/10 | 22.5 | 24.9 | 23.0 | 23.1 | 27.8 |
| 85/15 | 19.8 | 21.0 | 18.7 | 18.4 | 23.8 |
| 80/20 | 17.7 | 18.2 | 15.3 | 15.3 | 22.2 |
| 75/25 | 15.4 | 15.4 | 12.7 | 12.8 | 19.5 |
| 70/30 | 13.8 | 13.3 | 10.5 | 11.0 | ND |
| 65/35 | 11.3 | ND | ND | ND | ND |
| 60/40 | 10.1 | ND | ND | ND | ND |

*DBPA = 2,3-dibromopropyl acrylate
**BA = benzyl acrylate
***BMA = benzyl methacrylate
****PMA = phenyl methacrylate
*****BMAAM = benzylmethyl acrylamide

TABLE 3

Refractive Index (RI) Results For HEMA Copolymers

| Mole Ratio HEMA/ comonomer (mol/mol) | COMONOMER | | | |
|---|---|---|---|---|
| | POEM RI +/- std. dev. | PEM RI +/- std. dev. | POEA RI +/- std. dev. | PEA RI +/- std. dev. |
| 90/10 | 1.4732 +/- .0003 | 1.4727 +/- .0003 | 1.4676 +/- .0003 | 1.4671 +/- .0001 |
| 85/15 | 1.4847 +/- .0002 | 1.4844 +/- .0001 | 1.4771 +/- .0002 | 1.4770 +/- .0004 |
| 80/20 | 1.4940 +/- .0001 | 1.4941 +/- .0003 | 1.4853 +/- .0002 | 1.4853 +/- .0001 |
| 75/25 | 1.5021 +/- .0004 | 1.5019 +/- .0004 | 1.4927 +/- .0003 | 1.4923 +/- .0002 |
| 70/30 | 1.5094 +/- .0009 | 1.5094 +/- .0006 | 1.4990 +/- .0002 | 1.4991 +/- .0001 |
| 65/35 | 1.5152 +/- .0010 | 1.5151 +/- .0002 | 1.5049 +/- .0001 | 1.5050 +/- .0001 |
| 60/40 | 1.5204 +/- .0002 | 1.5206 +/- .0002 | 1.5104 +/- .0002 | 1.5107 +/- .0003 |

| Mole Ratio HEMA/ comonomer (mol/mol) | COMONOMER | | | | |
|---|---|---|---|---|---|
| | DBPA RI | BA RI | BMA RI | PMA RI | BMAAM RI |
| 95/5 | 1.4594 | 1.4582 | 1.4593 | 1.4594 | 1.4526 |
| 90/10 | 1.4694 | 1.4685 | 1.4741 | 1.4737 | 1.4625 |
| 85/15 | 1.4760 | 1.4785 | 1.4858 | 1.4870 | 1.4727 |
| 80/20 | 1.4813 | 1.4862 | 1.4954 | 1.4971 | 1.4801 |
| 75/25 | 1.4856 | 1.4945 | 1.5041 | 1.5072 | 1.4891 |
| 70/30 | 1.4933 | 1.5020 | 1.5119 | 1.5125 | ND |

IOLs manufactured using the hydrogel materials of the present invention can be of any design capable of being rolled or folded into a small cross section that can fit through a relatively small incision, i.e., 4.0 mm or less. For example, IOLs can be of a one-piece or multipiece design, and comprise optic and haptic portions. The optic portion is that portion which serves as the lens and the haptic portions are attached to the optic portion to hold the optic portion in proper alignment within an eye. The haptic portions may be integrally formed with the optic portion in a one-piece design or attached by staking, adhesives or other methods known to those skilled in the art in a multipiece design.

The subject IOLs may be manufactured to have the optic portion and the haptic portions made of the same or different materials. Preferably, in accordance with the present invention, the optic portion and the haptic portions are made of the same high-refractive index hydrogel material. However, the optic portion and the haptic portions may also be manufactured from different compositions and/or different formulations of the same composition as described in detail in U.S. Pat. Nos. 5,217,491 and 5,326,506, each incorporated herein in their entirety by reference. Once the particular hydrogel composition is selected, the material is cast in the form of rods and lathed into disks. These disks are then machined into IOLs. The IOLs are then cleaned, polished, packaged and sterilized by customary methods known to those skilled in the art.

In addition to IOLs, the materials of the present invention are also suitable for use as other ophthalmic devices such as contact lenses, keratoprostheses, capsular bag extension rings, corneal inlays, corneal rings or like devices.

IOLs manufactured using the unique materials of the present invention are used as customary in the field of ophthalmology. In a surgical procedure, an incision is placed in the cornea of an eye, most commonly the natural lens of the eye is removed and the IOL manufactured from materials of the present invention is inserted into the posterior chamber or lens capsule of the eye prior to closing the incision.

While there is shown and described herein certain specific structures and compositions of the present invention, it will be manifest to those skilled in the art that various modifications may be made without departing from the spirit and scope of the underlying inventive concept and that the same is not limited to particular structures herein shown and described except insofar as indicated by the scope of the appended claims.

I claim:

1. An intraocular lens manufactured from a composition comprising:
   an aromatic high refractive index monomer;
   a non-ultraviolet light absorbing hydrophilic monomer present in said composition in an amount greater than that of said high refractive index monomer;
   a hydrophobic ultraviolet light absorbing material;
   a crosslinker; and an initiator to form a hydrogel composition having a fully-hydrated water content of approximately 5 to 30 percent by weight and a fully-hydrated refractive index of approximately 1.45 or greater.

2. The intraocular lens of claim 1 wherein said composition includes a hydrophobic ultraviolet light absorbing material selected from the group consisting of beta-(4-benzotriazoyl-3-hydroxyphenoxy)ethyl acrylate, 4-(2-acryloxyethoxy)-2-hydroxybenzophenone, 4-methacryloxy-2-hydroxybenzophenone, 2-(2'-methacryloxy-5'-methylphenyl)benzotriazole, 2-(2'-hydroxy-5'-methacryoxyethylphenyl)2H-benzotriazole, 2-[3'-tert-Butyl-2'-hydroxy-5'-(3"-methacyloyloxypropyl)phenyl]5-chlorobenzotriazole, 2-(3'-tert-Butyl-5'-(3-dimethylvinylsilylpropoxy)2'-hydroxyphenyl]-5-methoxybenzotriazole, 2-(3'-Allyl-2'-hydroxy-5'-methylphenyl)benzotriazole, 2-[3'-tert-Butyl-2'-hydroxy-5'-(3"-methacryloyloxypropoxy)phenyl]-5-methoxybenzotriazole and 2-[3'-tert-Butyl-2'-hydroxy-5'-(3"-methacryloyloxypropoxy)phenyl]-5-chlorobenzotriazole.

3. The intraocular lens of claim 1 wherein said composition includes beta-(4-benzotriazoyl-3-hydroxyphenoxy)-ethyl acrylate as a hydrophobic ultraviolet light absorbing material.

4. The intraocular lens of claim 1 wherein said initiator is selected from the group consisting of azobis (isobutyronitrile), 2,2'-azobis(2,4-dimethylvaleronitrile), 2,2'-azobis(methylbutyronitrile), 1,1'-azobis (cyanocyclohexane), di-t-butyl peroxide, dicumyl peroxide, t-butylcumyl peroxide, 2,5-dimethyl-2,5-bis(2-ethylhexanoylperoxy)hexane, t-butylperoxyneodecanote, t-butyl peroxy 2-ethylhexanoate, di(4-t-butyl cyclohexyl) peroxydicarbonate, t-butyl peroxypivalate, decanoyl peroxide, lauroyl peroxide, benzoyl peroxide, 2,4-pentanedione peroxide, di(n-propyl)peroxydicarbonate, t-amyl peroxyneodecanoate and t-butyl peroxyacetate.

5. The intraocular lens of claim 1 wherein said initiator is azobis(isobutyronitrile).

6. The intraocular lens of claim 1 wherein said crosslinker is selected from the group consisting of ethylene glycol dimethacrylate, diethylene glycol dimethacrylate, triethylene glycol dimethacrylate and poly(ethylene glycol) dimethacrylate.

7. The intraocular lens of claim 1 wherein said crosslinker is ethylene glycol dimethacrylate.

8. The intraocular lens of claim 1 wherein said hydrophilic monomer is a monomer represented by the formula

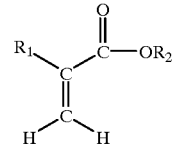

wherein $R_1$ is selected from the group consisting of hydrogen and $C_{1-6}$ alkyl, and $R_2$ is selected from the group consisting of hydrogen, an alkali metal, an alkaline earth metal, $C_{1-6}$ hydroxyalkyl, $C_{4-12}$ hydroxyalkoxyalkyl, $C_{4-12}$ hydroxydialkoxyalkyl, $C_{2-12}$ alkoxyalkyl, $C_{3-12}$ polyalkoxyalkyl, $C_{3-15}$ polyalkoxyhydroxyalkyl and $C_{2-12}$ dihydroxyalkyl.

9. The intraocular lens of claim 1 wherein said hydrophilic monomer is selected from the group consisting of 2-hydroxyethyl methacrylate, hydroxyethoxyethyl methacrylate, hydroxydiethoxyethyl methacrylate, methoxyethyl methacrylate, methoxyethoxyethyl methacrylate, methoxydiethoxyethyl methacrylate, poly(ethylene glycol) methacrylate, methoxy-poly(ethylene glycol) methacrylate, methacrylic acid, sodium methacrylate, glycerol methacrylate, hydroxypropyl methacrylate, and hydroxybutyl methacrylate.

10. The intraocular lens of claim 1 wherein said hydrophilic monomer is 2-hydroxyethyl methacrylate.

11. The intraocular lens of claim 1 wherein said high refractive index monomer is a monomer represented by one of the formulas

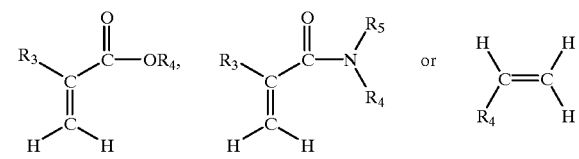

wherein $R_3$ is selected from the group consisting of hydrogen and $C_{1-6}$ alkyl, $R_4$ is selected from the group consisting of $C_{6-25}$ aryl, $C_{6-25}$ hydroxyaryl, $C_{6-25}$ aryloxyaryl, $C_{12-25}$ polyhydroxyaryl, $C_{12-35}$ polyaryl, $C_{6-15}$ arylalkyl, $C_{12-35}$ polyarylalkyl, $C_{6-15}$ alkoxyaryl, $C_{6-15}$ aryl halides, $C_{6-15}$ aryloxyalkyl, $C_{1-7}$ alkyl halides, $C_{6-15}$ arylthioalkyl, $C_{6-15}$ aryloxyalkyl halides and $C_{6-15}$ aryloxyalkoxyalkyl, and $R_5$ is selected from the group consisting of hydrogen, $C_{1-3}$ alkyl and $C_{6-15}$ alkylaryl.

12. The intraocular lens of claim 1 wherein said high refractive index monomer is selected from the group consisting of phenyl acrylate, phenyl methacrylate, benzyl acrylate, benzyl methacrylate, 2-phenylethyl acrylate, 2-phenylethyl methacrylate, 2-phenoxyethyl acrylate, 2-phenoxyethyl methacrylate, phenylthioethyl acrylate, phenylthioethyl methacrylate, 2,4,6-tribromophenyl acrylate, 2,4,6-tribromophenyl methacrylate, pentabromophenyl acrylate, pentabromophenyl methacrylate, pentachlorophenyl acrylate, pentachlorophenyl methacrylate, 2,3-dibromopropyl acrylate, 2,3-dibromopropyl methacrylate, 2-naphthyl acrylate, 2-naphthyl methacrylate, 4-methoxybenzyl acrylate, 4-methoxybenzyl methacrylate, 2-benzyloxyethyl acrylate, 2-benzyloxyethyl methacrylate, 4-chlorophenoxyethyl acrylate, 4-chlorophenoxyethyl methacrylate, 2-phenoxyethoxyethyl acrylate, 2-phenoxyethoxyethyl methacrylate, N-phenyl acrylamide, N-phenyl methacrylamide N-benzyl acrylamide N-benzyl methacrylamide N,N-dibenzyl acrylamide N,N-dibenzyl methacrylamide N-diphenylmethyl acrylamide, N-(4-methylphenyl)methyl acrylamide N-1-naphthyl acrylamide N-4-nitrophenyl acrylamide, N-(2-phenylethyl) acrylamide N-triphenylmethyl acrylamide, N-(4-hydroxyphenyl) acrylamide, N,N-methylphenyl acrylamide N,N-phenyl phenylethyl acrylamide N-diphenylmethyl methacrylamide, N-(4-methyl phenyl)methyl methacrylamide N-1-naphthyl methacrylamide, N-4-nitrophenyl methacrylamide, N-(2-phenylethyl) methacrylamide N-triphenylmethyl methacrylamide, N-(4-hydroxyphenyl) methacrylamide N,N-methylphenyl methacrylamide, N,N'-phenyl phenylethyl. methacrylamide N-vinylcarbazole, 4-vinylpyridine, 2-vinylpyridine, styrene, 2-chlorostyrene, 3-chlorostyrene, 4-chlorostyrene, 2-bromostyrene, 3-bromostyrene, 4-bromostyrene, 2,6-dichlorostyrene, 2-iodostyrene, 3-iodostyrene, 4-iodostyrene, pentabromostyrene, 4-phenylstyrene, 1-vinylnaphthalene, 2-vinylnaphthalene, 9-vinylanthracene and 4-phenoxystyrene.

13. The intraocular lens of claim 1 wherein said high refractive index monomer and said hydrophilic monomer comprise at least about 70 percent by weight of said composition.

14. The intraocular lens of claim 1 wherein said high refractive index monomer and said hydrophilic monomer comprise approximately 75 percent by weight of said composition.

15. The intraocular lens of claim 1 wherein said hydrophilic monomer is 2-hydroxyethyl methacrylate and said high refractive index monomer is phenyl methacrylate.

16. The intraocular lens of claim 1 wherein said hydrophilic monomer is 2-hydroxyethyl methacrylate and said high refractive index monomer is benzyl acrylate.

17. The intraocular lens of claim 1 wherein said hydrophilic monomer is 2-hydroxyethyl methacrylate and said high refractive index monomer is benzyl methacrylate.

18. The intraocular lens of claim 1 wherein said hydrophilic monomer is 2-hydroxyethyl methacrylate and said high refractive index monomer is 2-phenylethyl acrylate.

19. The intraocular lens of claim 1 wherein said hydrophilic monomer is 2-hydroxyethyl methacrylate and said high refractive index monomer is 2-phenylethyl methacrylate.

20. The intraocular lens of claim 1 wherein said hydrophilic monomer is 2-hydroxyethyl methacrylate and said high refractive index monomer is 2-phenoxyethyl acrylate.

21. The intraocular lens of claim 1 wherein said hydrophilic monomer is 2-hydroxyethyl methacrylate and said high refractive index monomer is 2-phenoxyethyl methacrylate.

22. The intraocular lens of claim 1 wherein said hydrophilic monomer is 2-hydroxyethyl methacrylate and said high refractive index monomer is N-benzyl methacrylamide.

23. The intraocular lens of claim 1 wherein said hydrophilic monomer is 2-hydroxyethyl methacrylate and said high refractive index monomer is N-vinylcarbazole.

* * * * *